United States Patent [19]

Nite

[11] 3,966,905
[45] June 29, 1976

[54] STABILIZED CATECHOL AMINE SOLUTIONS

[75] Inventor: Rebecca F. Nite, Sunnyvale, Calif.

[73] Assignee: Barnes-Hind Pharmaceuticals, Inc., Sunnyvale, Calif.

[22] Filed: Nov. 25, 1974

[21] Appl. No.: 526,660

Related U.S. Application Data

[63] Continuation of Ser. No. 365,013, May 29, 1973, abandoned.

[52] U.S. Cl. .................................. 424/80; 424/330
[51] Int. Cl.² .......................................... A61K 31/135
[58] Field of Search .............................. 424/80, 330

[56] References Cited
UNITED STATES PATENTS

| | | | |
|---|---|---|---|
| 3,149,035 | 4/1961 | Riegelman | 424/175 |
| 3,311,577 | 3/1967 | Rankin | 424/80 |
| 3,557,280 | 1/1971 | Weber et al. | 424/80 |
| 3,634,586 | 1/1972 | Kaser et al. | 424/80 |
| 3,755,561 | 8/1973 | Rankin | 424/80 |

FOREIGN PATENTS OR APPLICATIONS 4,549m  11/1966  France .......................... 424/80

OTHER PUBLICATIONS

Handbook of Non-Prescription Drugs, 1973 Edition Published APHA, 3/1973 pp. 102–106.
Hecht et al., Chemical Abstracts 75:80294k (1971).
Fujita et al., Chemical Abstracts 76:27949x (1972).
Chemical Abstracts 76:37440p (1972).

Primary Examiner—Norman A. Drezin
Attorney, Agent, or Firm—Townsend and Townsend

[57] ABSTRACT

Catechol amine solutions for physiological uses at mild pHs are provided, employing in combination a catecholalkyl amine, boric acid, a polyvinylpyrrolidone polymer and a physiologically acceptable antioxidant. The solutions are formulated in aqueous media and have greatly enhanced storage life, with substantially reduced susceptibility to light induced and oxidative degradation.

5 Claims, No Drawings

STABILIZED CATECHOL AMINE SOLUTIONS

This is a continuation of application Ser. No. 365,013, filed May 29, 1973, now abandoned.

BACKGROUND OF THE INVENTION

1. Field of the Invention

Catechol amine solutions, particularly epinephrine and modifications thereof, have wide application for medicinal purposes. One application for epinephrine is the use in the treatment in ophthalmological diseases, such as glaucoma. Because of the extreme sensitivity of the eye to irritation by relatively mild aqueous acid or base, as well as numerous chemical irritants, any physiologically useful solution should be substantially non-irritating to the eye.

Epinephrine is a catecholhydroxyalkyl amine. The catechol compounds are particularly sensitive to oxidation to o-quinones, which can react further to form highly colored compounds. In fact, epinephrine can react to form adrenochrome, a highly colored indole derivative.

The modification or degradation of the catechol amines is undesirable for a number of reasons. Modification of the catechol amine results in loss of titer of the active ingredient, formation of compounds which may have undesirable physiological effects, and the appearance of a dark color, which makes the solution offensive and unmarketable.

The manner of use of a solution for eye treatment maintains an aerobic or oxidative environment. Normally, an eye dropper is used and treatment is carried out on a periodic basis. Therefore, for each treatment, air is in contact with the solution and the oxygen in the solution replenished. Even in a brown bottle, the solution will be repeatedly exposed to light, which may initiate reactions which may then proceed in the dark.

2. Description of the Prior Art

U.S. Pat. No. 3,149,035 employs bisulphite and boric acid in combination with catechol amines to enhance stability of the catechol amines. French Pat. No. 4.549 M discloses improved stability of therapeutic amine solutions containing polyvinylpyrrolidone, by insuring the removal of monomer and any aldehydes which may be adventitiously present in the commercially available polyvinylpyrrolidone.

DESCRIPTION OF THE SPECIFIC EMBODIMENTS

Stabilized physiologically useful solutions of catechol alkyl amines, particularly beta-amino, are provided by employing in an aqueous medium in combination a catechol amine, borate, a small but effective amount of polyvinylpyrrolidone polymer and a physiologically acceptable antioxidant, at a substantially neutral or mildly basic pH.

The individual components of the composition will be considered first. The first ingredient is a catechol alkyl amine. These compounds will have the alkyl substituent at the 4 position of the ring, will normally have a beta amino group and will be of from 8 to 12 carbon atoms. The amino group may be either primary or secondary. There may be from zero to one hydroxyl group bonded to the alkyl substituent on other than a carbon bonded to nitrogen.

For the most part, the compounds employed will come within the vollowing formula:

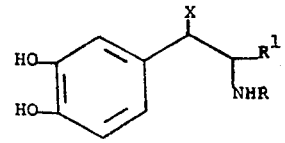

wherein R and $R^1$ are hydrogen or alkyl of from 1 to 3 carbon atoms, $R^1$ usually of from 1 to 2 carbon atoms, usually R is hydrogen, methyl, ethyl, propyl or isopropyl and $R^1$ is hydrogen methyl or ethyl; and X is hydrogen or hydroxyl.

Included in the aqueous medium will be a small amount of borate, which serves not only to react with the catechol amines to form a soluble borate complex, but also acts as a buffer for the system, to maintain the desired pH.

The third ingredient is a polyvinylpyrrolidone polymer having from zero to 30 number percent of another monomer, e.g., vinyl acetate. The polyvinylpyrrolidone is preferably a homopolymer, is commercially available, and will normally have a viscosity average molecular weight in the range of about $1-10 \times 10^4$.

The final ingredient which is employed is a physiologically acceptable antioxidant. Various antioxidants include ascorbic acid, erythorbic acid (isoascorbic acid), acetylcysteine and thioglycerol. The preferred antioxidant is erythorbic acid.

In order to obtain the desired pH, the addition of a small amount of an alkali metal hydroxide will be employed, particularly alkali metals of atomic number 11 to 19, and normally sodium. The initial pH will be from about 5.5 to 8.5, usually from about 6.5 to 7.5.

The solutions employed will normally be dilute aqueous solutions having less than about 15 total weight percent of the above additives, usually less than about 12 total weight of the additives, and generally more than about 0.5 total weight percent of the additives, usually more than about 2 total weight percent of the additives.

The amounts of the various materials may be varied relatively widely. (Unless otherwise indicated, the weight percent is based on the final composition). The catechol amine, which includes such compounds as epinephrine, levarterenol and nordefrin, will normally be present in at least about 0.1 weight percent, usually at least about 0.5 weight percent, generally not exceeding 10 weight percent, usually not exceeding 5 weight percent. Preferably, with epinephrine, the amount will be about 0.5 to 2 weight percent. Preferably, the catechol amine will be present in about 0.5 to 3 weight percent.

The borate which is present will generally be present in from about 0.1 to 2.5 weight percent (reported as boric acid), preferably from about 0.5 to 2.0 weight percent. The mole ratio of borate to catechol amine will generally be from about 0.5–6:1 usually from about 1.5–4:1.

The polyvinylpyrrolidone polymer will be present in amounts varying from about 0.1 to 5 weight percent, more usually from about 0.5 to 3 weight percent.

Depending on the antioxidant, the amount of antioxidant may vary from about 0.25 to 5 weight percent, more usually from about 0.5 to 3 weight percent.

Other additives may also be included such as preservatives, chelating agents, and the like, individually being present in amounts from about 0.01 to 0.5 weight percent. Water will then be employed, to bring the total amount of the composition to 100 weight percent.

In order to demonstrate the effectiveness of the subject composition in having greatly extended shelf lifetimes and stability to light induced oxidative degradation, a number of experiments were carried out.

The test procedures which were employed are as follows:

Oxidation Method A: An 8 ml quantity of each of the experimental solutions is placed in 10 ml Kimax test tubes in a test tube rack. The solutions are exposed to the air and to exaggerated lighting from fluorescent bulbs at a distance of approximately 1.5 feet in a light cabinet. The results are reported as time for solution to assume a visible red coloration.

Oxidation Method B: With the use of fish bowl pumps, air is continuously bubbled into 100 ml of each solution in individual Erlenmeyer flasks. These solutions are exposed to light from overhead fluorescent lights from a distance of approximately eight feet. Evaporated water is replenished every day. The time for each solution to assume the visible red coloration is noted down. Assays are conducted before and after the bubbling treatment.

The following results compare a solution containing epinephrine, boric acid and sodium bisulphite, a solution containing epinephrine, boric acid and erythorbic acid, two commercially available solutions, as well as one solution coming within the subject invention.

TABLE I+

| Formula | A | B | C |
|---|---|---|---|
| Epinephrine | 1 | 1 | 1 |
| Boric Acid | 1 | 2 | 2 |
| Polyvinylpyrrolidone* | 2.5 | — | — |
| Erythorbic acid | 1.5 | — | 1.5 |
| Sodium bisulfite | — | 0.4 | — |
| pH | 7.4 | 7.4 | 7.4 |

Days Till Coloration

| Oxidation Method | Formula A | B | C | Commercial Formulation 1 | 2 |
|---|---|---|---|---|---|
| A | 75 | 10 | 54 | 9 | 28 |
| B | 82 | 7 | 53 | 10 | 19 |

+Amounts reported in grams/100 ml (w/v).
*Plasdone c,~40,000 viscosity average molecular weight.

It is quite evident from the above results, that the formulation of the subject invention —A— is far superior to any of the other formulations, including the two commercially available formulations.

In the following experiment, three formulations were tested, one coming within the subject invention, one a commercial formulation, and one differing from the subject invention in lacking polyvinylpyrrolidone. The experiment was carried out for 60 days, at the end of which time, the percent of epinephrine still present was determined by light absorption at 480nm.

The following table indicates the results.

TABLE II*

| Formula | D | E |
|---|---|---|
| Epinephrine | 1 | 1 |
| Boric Acid | 1 | 1 |
| Polyvinylpyrrolidone | 1 | — |
| Erythorbic acid | 1.5 | 1.5 |
| pH | 7.4 | 7.4 |

| Oxidation Method | % of original epinephrine present on 60th day | | |
|---|---|---|---|
| | D | E | Commercial Formulation 1 |
| A | 98 | 92 | 52 |
| B | 98 | 78 | 84 |

*Amounts reported in grams/100 ml (w/v).

Except for the commercial formula, there was no coloration at the time of the epinephrine determination. A dark reddish-brown coloration occurred in this formula within 10 days. The above table further substantiates the excellent stability of the subject compositions, as exemplified by D, in that there is substantially no change in the epinephrine concentration despite the extreme conditions to which the compositions were subjected.

Long term studies were also carried out, whereby the subject compositions were allowed to stand for long periods of time under normal storage conditions and then used in the normal manner by removing small aliquots of the solution by means of an eye dropper. After 9 months of storage at 25°C and 2 months of usage, a formulation containing 1 weight percent epinephrine, 1 weight percent boric acid 2.5 weight percent polyvinylpyrrolidone, and 1.5 weight percent erythorbic acid at a pH of 7.1, showed substantially no change in the epinephrine titer. A commercial formulation showed an epinephrine titer of only 78% of the original titer.

The above results clearly evidence that a combination of epinephrine, boric acid polyvinylpyrrolidone and erythorbic acid greatly extends the useful storage life and life during usage of physiologically useful epinephrine solutions. These results demonstrate that catechol alkyl amines can be maintained in physiologically useful solutions at constant concentration and as clear commercially acceptable solutions for long periods of time.

Although the foregoing invention has been described in some detail by way of illustration and example for purposes of clarity of understanding, it will be obvious that certain changes and modifications may be practiced within the scope of the appended claims.

What is claimed is:

1. A physiologically useful catechol amine solution having enhanced stability comprising:
   in an aqueous medium from 0.1 to 10 weight percent of a catechol alkyl amine of from 8 to 12 carbon atoms of the formula:

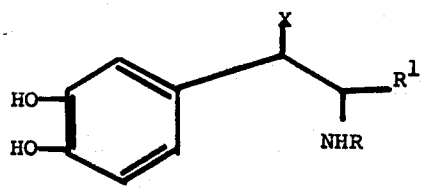

wherein R and $R^1$ are hydrogen or alkyl of from 1 to 3 carbon atoms, and X is hydrogen or hydroxyl;
from 0.1 to 5 weight percent of polyvinylpyrrolidone of a molecular weight in the range of about 1–10 × $10^4$ and from 0.1 to 2. weight percent of boric acid as borate, and a physiologically acceptable antioxidant selected from the group consisting of ascorbic acid, erythorbic acid, acetylcysteine and thioglycerol in an amount of from about 0.2 to 5 weight percent at a pH in the range of about 5.5 to 8.5.

2. A composition according to claim 1 having from 0.5 to 3 weight percent of a physiologically acceptable antioxidant.

3. A composition according to claim 2, wherein said antioxidant is erythorbic acid.

4. A composition according to claim 1 containing from 0.5 to 2 weight percent of epinephrine, about 0.5 to 1.5 weight percent boric acid and at a pH in the range of about 6.5 to 7.5.

5. A physiologically useful catechol amine solution having enhanced stability comprising:
in an aqueous medium from about 0.5 to 2 weight percent of epinephrine, from about 0.5 to 2 weight percent of boric acid as borate from about 0.5 to 3 weight percent of polyvinylpyrrolidone, and from 0.5 to 2.5 weight percent erythorbic acid at a pH in the range of about 6.5 to 7.5.

* * * * *